US005893871A

United States Patent [19]

Tanaka

[11] Patent Number: 5,893,871

[45] Date of Patent: Apr. 13, 1999

[54] HEALTH PROMOTING IMPLEMENT HAVING ACUPRESSURE EFFECT AND CAPABLE OF EASY ATTACHMENT/ DETACHMENT AND REPEATING USE

[75] Inventor: Nobutaka Tanaka, Daito, Japan

[73] Assignee: Tanaka Planning Corporation, Osaka, Japan

[21] Appl. No.: 08/763,083

[22] Filed: Dec. 10, 1996

[30] Foreign Application Priority Data

| | | | |
|---|---|---|---|
| Dec. 12, 1995 | [JP] | Japan | 7-323375 |
| Apr. 10, 1996 | [JP] | Japan | 8-088108 |

[51] Int. Cl.$^6$ .......... A61B 17/00

[52] U.S. Cl. .......... 606/204

[58] Field of Search .......... 606/204, 201; 601/134–135

[56] References Cited

U.S. PATENT DOCUMENTS

| | | | |
|---|---|---|---|
| 2,524,326 | 10/1950 | Murphy . | |
| 2,806,470 | 8/1957 | Ferrier | 601/135 |
| 4,411,258 | 10/1983 | Pujals, Jr. | 601/134 |
| 4,577,622 | 3/1986 | Jennings | 601/134 |
| 4,944,289 | 7/1990 | Matthews | 601/134 |
| 5,290,307 | 3/1994 | Choy | 606/204 |
| 5,470,304 | 11/1995 | Decanto | 606/204 X |

FOREIGN PATENT DOCUMENTS

| | | |
|---|---|---|
| 0100050 | 2/1994 | European Pat. Off. . |
| 0630638 | 12/1994 | European Pat. Off. . |
| 1124140 | 10/1956 | France . |
| 9417221 | 1/1995 | Germany . |
| 4400496 | 7/1995 | Germany . |

*Primary Examiner*—Michael Buiz
*Assistant Examiner*—Vikki Trinh
*Attorney, Agent, or Firm*—Rabin & Champagne, P.C.

[57] ABSTRACT

A wrist band according to the present invention includes a band body which is fitted on the body in a freely fitted and removable manner to surround part of the body, and a projection provided on the surface of the band body on the side facing the body. When the wrist band is fitted around the wrist, the projection, formed like a lattice on its inner surface, abuts on the hand joint region. Then, the band body surrounds the entire wrist and the projection is pressed against the hand joint region by the elastic force of the band body. Thus, the projection pressed against the hand joint region provides an acupressure effect.

28 Claims, 10 Drawing Sheets

HEALTH PROMOTING IMPLEMENT HAVING ACUPRESSURE EFFECT AND CAPABLE OF EASY ATTACHMENT/DETACHMENT AND REPEATING USE

BACKGROUND OF THE INVENTION

1. Field of the Invention

The present invention relates to health promoting implements, and particularly to a health promoting implement which is used for the purpose of reducing pains in joints and muscles in arms or legs or the purpose of maintaining and promoting health conditions of the joint regions and the like.

2. Description of the Background Art

The technique of so-called taping is known, which is for treating troubles in joints or muscles accompanied by pain by sticking adhesive tape on the troubled parts or on corresponding effective spots for applying the acupressure, which is performed in osteopaths' offices and the like. (Acupressure: a practice analogous to acupuncture but involving the application of manual pressure to parts of the body rather than the insertion of needles. Called "shiatsu" in Japanese. An effective spot for the acupressure is called "tsubo" in Japanese.)

FIG. 15 shows the taping technique applied on the wrist. In this figure, a plurality of adhesive tapes 9*a*, 9*b* having a width of about 3 mm are stuck in a lattice-like form on a painful part or effective spots for the treatment on the wrist. Similarly, when adhesive tapes are stuck in a lattice or a spiral form on a painful part of the leg or arm, for example, the adhesive tapes stimulate the painful part or the corresponding effective spots for the treatment and its acupressure effect reduces the pain. (For example, refer to "Spiral Taping", written by Nobutaka Tanaka, published on Nov. 1, 1991 in Japan.)

However, in the taping technique, the adhesive tapes are difficult to handle because of their adhesiveness. Furthermore, the adhesive may cause a rash on the skin depending on the constitution of the patient. Moreover, since the adhesive tapes removed from the body can not be reused, they must be discarded. Therefore it is necessary to prepare and use new adhesive tapes every time a treatment is performed.

SUMMARY OF THE INVENTION

An object of the present invention is to provide a health promoting implement which avoids the trouble of sticking difficult-to-handle adhesive tape on the body.

Another object of the present invention is to provide a health promoting implement which eliminates the possibility of a rash on the skin.

Still another object of the present invention is to provide a health promoting implement which can be freely attached on/detached from the body so that it can be repeatedly used.

In order to achieve the objects above, a health promoting implement according to a certain aspect of the present invention includes a band body which is fitted on the body in a freely fitted and removable manner to surround a part of the body, and a projection provided on the surface of the band body on the side which faces the body.

According to the health promoting implement constructed as stated above, when the band body is so fitted around the arm or the like that the projection provided on the surface of the band body abuts on a painful portion or a corresponding effective spot, the projection presses and stimulates the effective spot to provide an acupressure effect.

The band body may include a cylindrical body formed of cloth having elasticity When the cylindrical body is bent about at the center seen from the side, it is formed into a shape suitable for application on a bending portion such as the knee and the elbow. The band body may be formed of a flexible band body having on its both ends a male member and a female member of a plane fastener which can be coupled while overlapped.

The projection may include at least one linear rib, two linear ribs intersecting each other, two linear ribs parallel to each other, or a linear rib extending in a predetermined direction.

According to a health promoting implement of another aspect of the present invention, the health promoting implement described above further includes positioning means for positioning the projection in the position where it abuts on the body. Specifically, the positioning means may include a through hole which is formed in the band body and fits around a projecting part of a bent part of the elbow, the kneecap, and the like. According to this device, the positioning means determines the position where the projection abuts on the body. Therefore, when the band body is put on the arm, for example, the projection naturally comes in contact with a target portion of the acupressure.

As explained above, according to one aspect of the present invention, a health promoting implement is provided which can apply acupressure to effective spots or painful parts just as worn on some part of the body, such as the arm, the leg, and so forth. This eliminates the necessity of the troublesome work of sticking the difficult-to-handle adhesive tapes on the body, which has been necessary in the taping explained above.

Furthermore, unlike the conventional process, the present invention uses no adhesive tape and therefore it solves the problem of a rash on the skin caused by the adhesive agent.

Moreover, since the health promoting implement of the present invention can be freely attached on and detached from the body, it can be repeatedly used, unlike the aforementioned taping technique in which adhesive tapes removed from the body must be discarded.

According to the health promoting implement of the other aspect of the present invention, when the health promoting implement is fitted on the body, the projection naturally comes to the portion which is a target of the acupressure, resulting in accurate acupressure to the effective spots.

Even when the body has no disease, the use of the health promoting implement of the present invention maintains and promotes the health condition of the joint parts and the like where it is applied through the acupressure effect by the projection, thus providing the above-mentioned effects as well.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
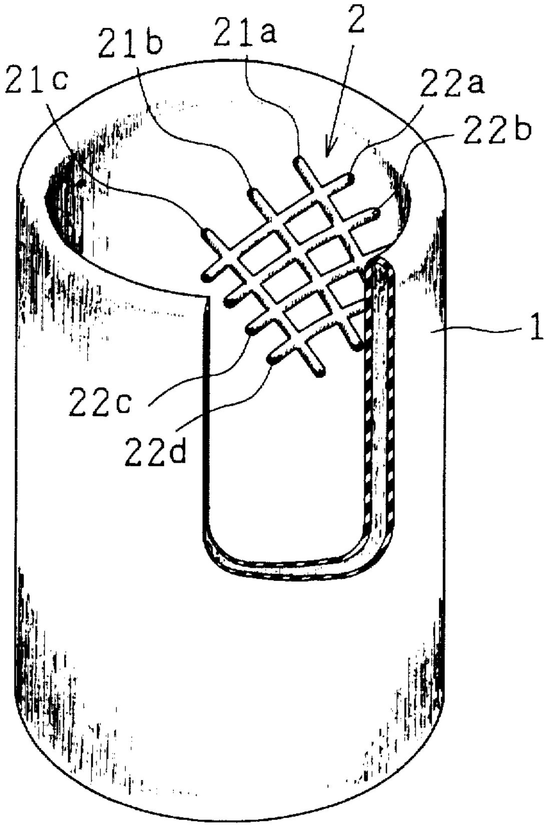
FIG. 1 is a partially broken perspective view of a wrist band according to a first embodiment of the present invention.
Figure 2:
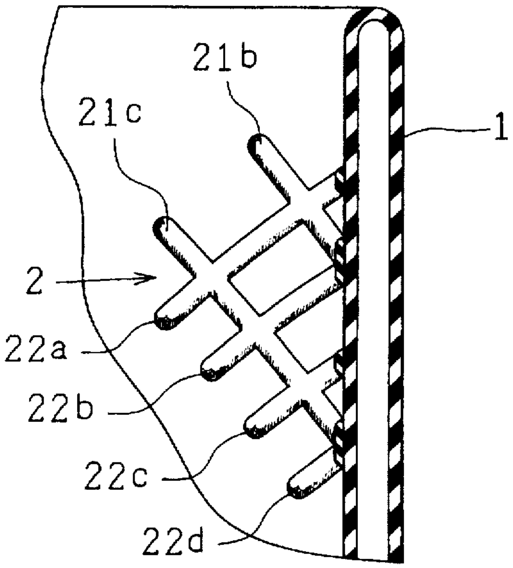
FIG. 2 is a cross-sectional view of the main part of the wrist band of FIG. 1.

FIGS. 1 and 2 show a wrist band according to a first embodiment of the present invention, which is fitted around the wrist in use.

A band body 1 is formed into a cylindrical shape using cloth having excellent elasticity, which has a projection (a raised part) 2 about 1 mm high on its inside surface.

In this embodiment, the projection 2 includes a group of linearly extending first ribs 21*a*, 21*b* and 21*c* and a group of second ribs 22*a*, 22*b*, 22*c* and 22*d* intersecting like a lattice.

Figure 3:
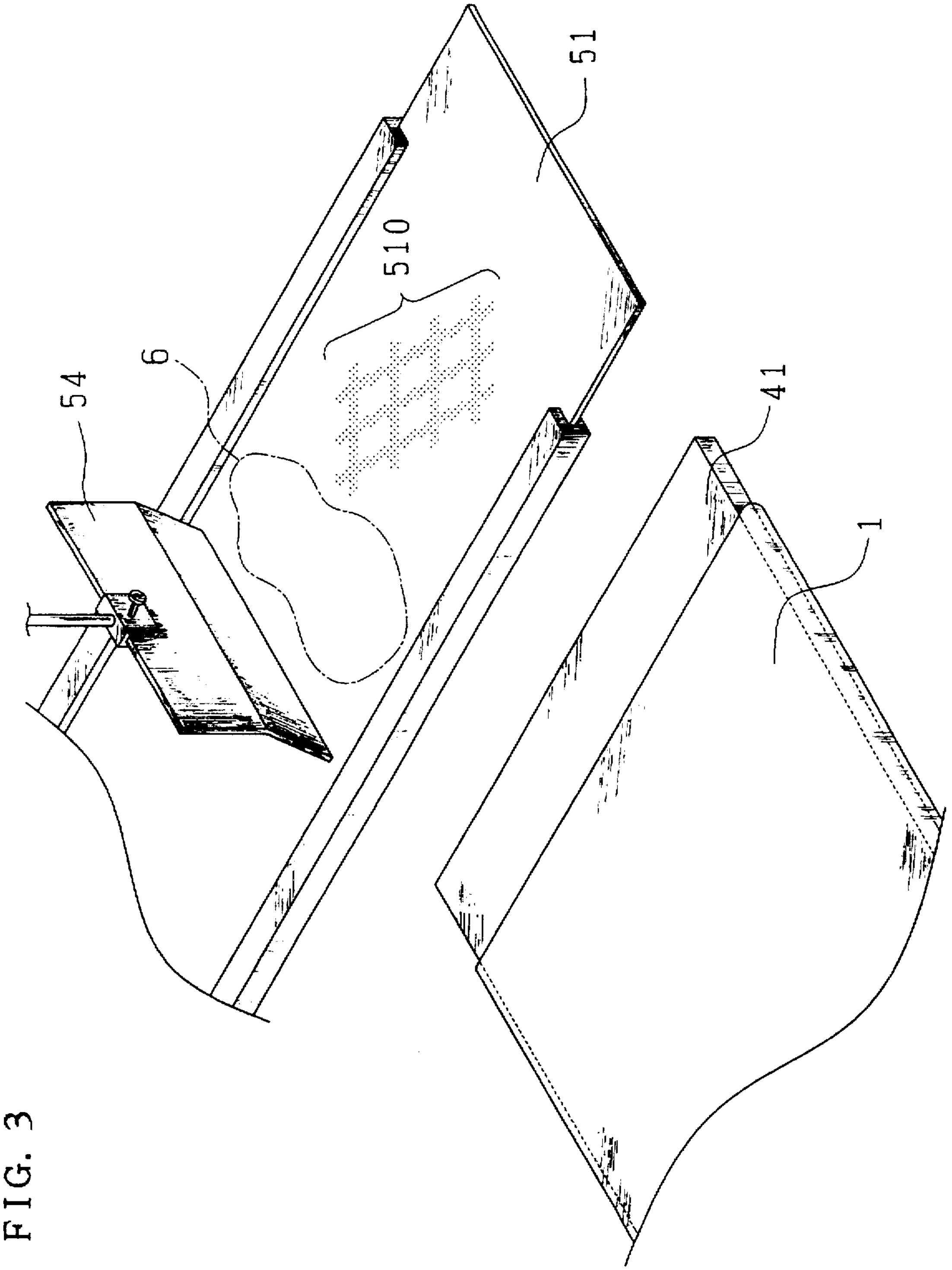
FIG. 3 is a diagram illustrating the process of forming the projection 2 on the wrist band of FIG. 1.

The projection 2 is formed on the inside surface of the band body 1 by using the device shown in FIG. 3.

This device includes a plate-like arm 41 for holding the band body 1, a plate 51 having a group of fine holes 510 formed in the region shaped like a lattice, and a spatula 54 which slides on the upper surface of the plate 51.

When forming the projection 2 on the band body 1, the band body 1, turned inside out, is fitted around the plate-like arm 41 and paste-like silicone 6 is supplied on the plate 51 in front of the spatula 54. Next, the plate-like arm 41 is moved under the plate 51 and the band body 1 is brought into contact with the back side of the group of fine holes group 510. In this condition, the spatula 54 is moved to press out the paste-like silicone 6 through the group of fine holes group 510 onto the band body 1 so that it attaches on the surface of the band body 1. Then the silicone 6 attached there is heated and dried to form the projection 2 having proper elasticity on the band body 1. This band body 1 is turned over again and then the wrist band shown in FIG. 1 is completed.

The lattice-like projection 2 is formed in a position which is suitable for applying pressure to the hand joint region (i.e., wrist) between the arm and the palm when the wrist band is worn.

When the wrist band is worn around the wrist and the lattice-like projection 2 formed on its inside surface abuts on the hand joint region, the band body 1 surrounds the entire wrist and the elasticity of the band body 1 presses the projection 2 against the hand joint region. That is to say, an acupressure (shiatsu) effect is obtained as the projection 2 is pressed against the hand joint region. Accordingly, if that region is painful because of a problem in the hand joint, the acupressure effect reduces the pain. Also, the acupressure effect stimulates the effective spots for the treatment (tsubo) in the hand-joint region to maintain and promote the health condition of that region.

Figure 4:
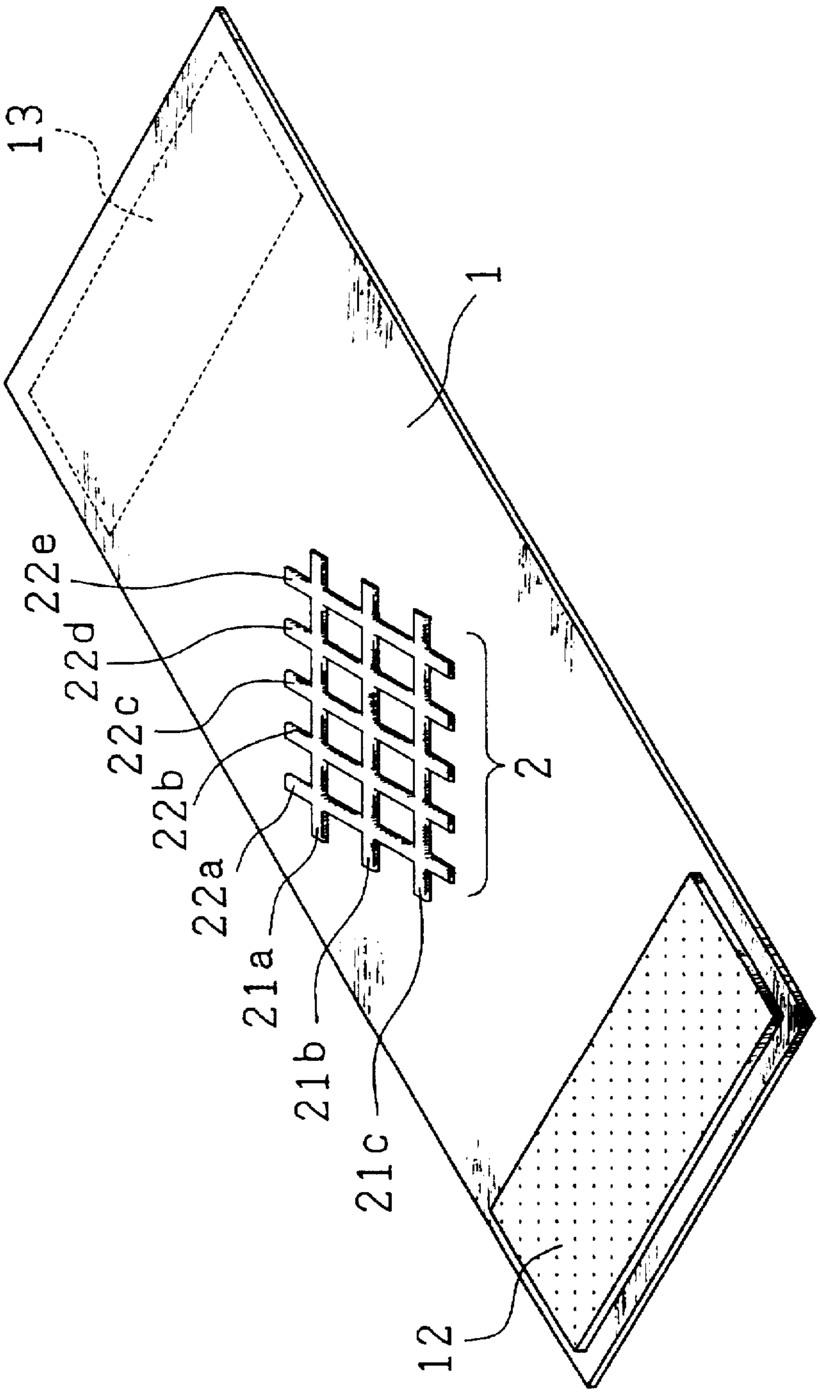
FIG. 4 is a developed perspective view of a wrist band according to a second embodiment of the present invention.

FIG. 4 shows a wrist band according to a second embodiment of the present invention, which has a band body 1 formed of band cloth having no elasticity. In this embodiment, a male member 12 of a plane fastener is sewn on one end of one side of the band body 1 and a female member 13 of the plane fastener is sewn on the other end of the other side. Similarly to the wrist band of the first embodiment, the band body 1, too, has on its one side a projection 2 including the first ribs 21*a*, 21*b* and 21*c* and the second ribs 22*a*, 22*b*, 22*c*, 22*d* and 22*e* intersecting like a lattice.

With the wrist band of this embodiment, when the band body 1 is wound around the wrist and then the male and female members 12 and 13 of the plane fastener provided on its both ends are laid on top of the other, it is fitted around the wrist and the projection 2 on the inside surface of the band body 1 effects the acupressure effect, in the same way as that explained above.

Figure 5:
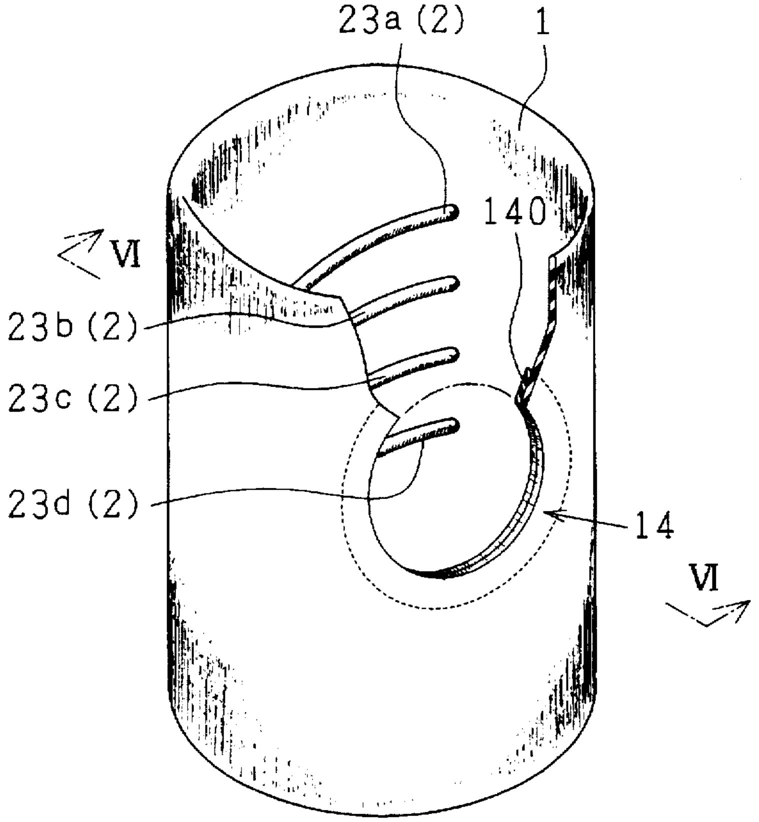
FIG. 5 is a partially broken perspective view of a knee supporter according to a third embodiment of the present invention.
Figure 6:
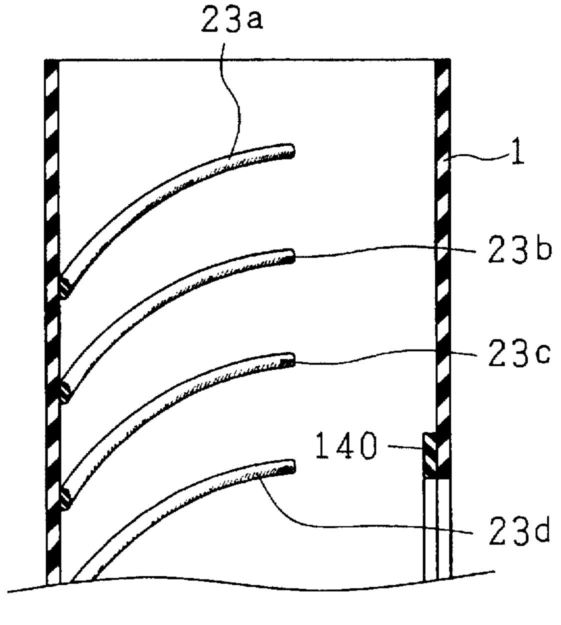
FIG. 6 is a cross-sectional view of the important part along the line VI—VI in FIG. 5.

FIG. 5 is a partially broken perspective view of a knee supporter according to a third embodiment of the present invention. FIG. 6 is a cross-sectional view of its main part taken along the line VI—VI in FIG. 5. As shown, each rib has a hemispherical cross-sectional profile.

As shown in FIG. 5, a cylindrical band body 1 formed of cloth having excellent elasticity has a through hole 14 which fits around the kneecap for positioning. It also has ribs 23*a*, 23*b*, 23*c* and 23*d* which are made of silicone resin having elasticity and arranged in parallel to each other in a position opposing the through hole 14 on the inside surface of the band body 1. The ribs 23*a*, 23*b*, 23*c* and 23*d* are oriented in a direction inclined with respect to the length of the cylindrical band body 1 so that the ribs 23*a*, 23*b*, 23*c* and 23*d* come in contact with the skin in a spiral manner when the band body is fitted around the knee. As to the width, the intervals and the number of the ribs 23*a*, 23*b*, 23*c* and 23*d*, considering the distribution of the effective spots located on the back of the knee, that it is preferred to provide four ribs having a width of about 5 mm and a length of about 13 cm at intervals of about 1.5 cm.

Figure 10:
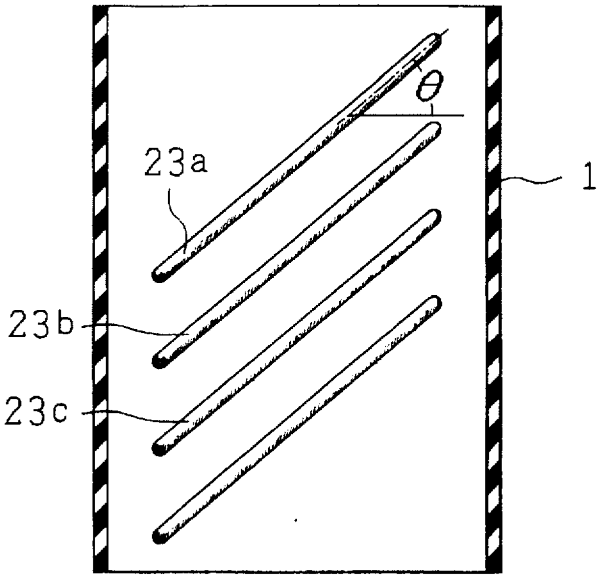
FIG. 10 is a diagram for illustrating the angle of inclination of the ribs 23*a*, 23*b*, 23*c* formed on the knee supporter according to the embodiment of FIG. 5.

Furthermore, it is preferred that the ribs 23*a*, 23*b*, 23*c* and 23*d* are inclined with respect to the width of the band body 1 at an angle $\theta$ in the range of 30 to 45 degrees, with the band body 1 so arranged that the through hole 14 is located in the center of the front (Refer to FIG. 10.).

Moreover, a circular rib 140 formed of silicone resin is also formed on the periphery of the through hole 14 on the inner side of the band body 1. In this embodiment, the ribs 23*a*, 23*b*, 23*c* and 23*d* and the circular rib 140 correspond to the projection 2 constituting the invention. The circular rib 140 is formed of silicone having elasticity, and abuts on the periphery of the kneecap when the knee supporter is worn. The through hole 14 is fitted around the kneecap to prevent excessive stimulation from being applied to the periphery of the kneecap. This is due to the fact that excessive stimulation to the pain-sensitive joint cover around the patella forming the kneecap increases the pain. The circular rib 140 prevents fibers in the periphery of the through hole 14 from fraying.

Figure 7:
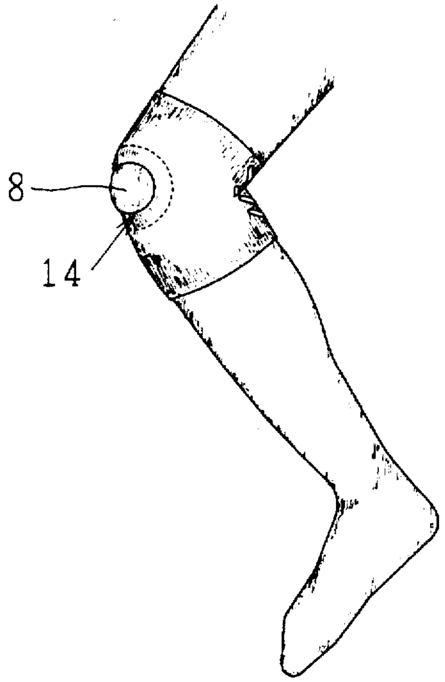
FIG. 7 is a perspective view of the knee supporter of FIG. 5 fitted around the knee.

As shown in FIG. 7, when the knee supporter of FIG. 5 is put on the knee, the through hole 14 fits around the kneecap 8, and then the ribs 23*a*, 23*b*, 23*c* and 23*d*, or the projection 2, applies pressure to the effective spots (tsubo), called "Ichu", "Kyokusen", "Inkoku" located on the back of the knee. Accordingly, if the knee joint has a problem, the pain is reduced by the acupressure effect. Even if the knee joint has no problems, the acupressure effect maintains and promotes the health condition of the joint region. In the knee supporter explained above, the through hole 14 fits around the kneecap to provide the positioning function, but the through hole 14 is not necessarily required if the circular rib 140 is raised high so that the circular rib 140 fits around the kneecap. In this case, the circular rib 140 functions as the positioning means constituting the invention.

Figure 8:
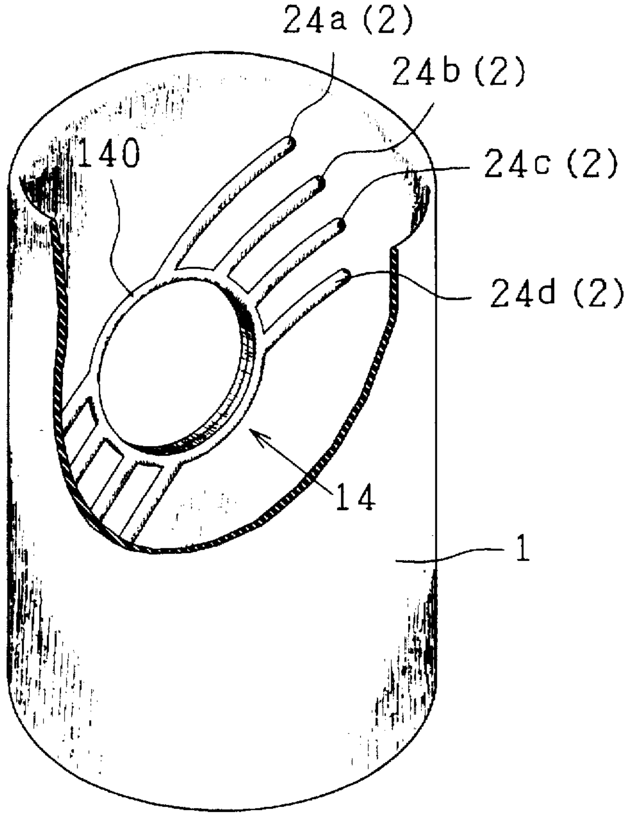
FIG. 8 is a partially broken perspective view of a knee supporter according to a fourth embodiment of the present invention.

FIG. 8 is a partially broken perspective view of a knee supporter according to a fourth embodiment of the present invention, seen from the back of the knee. The band body 1 is formed in a cylindrical form with cloth having elasticity like that described above. The band body has ribs 24*a*, 24*b*, 24*c* and 24*d* linearly extending from the periphery of the through hole 14 around which the circular rib 140 is formed. The circular rib 140 and the ribs 24*a*, 24*b*, 24*c*, 24*d* are formed by applying flexible silicone resin, in the same way as the embodiments already explained. Then the ribs 24*a*, 24*b*, 24*c* and 24*d* function to press the effective spots, called "Ryokyu", "Sanri", located near the kneecap.

Furthermore, it is preferred that the ribs 24*a*, 24*b*, 24*c* and 24*d* are inclined with respect to the width direction of the band body 1 at an angle between about 30 and 45 degrees with the band body 1 so arranged that the through hole 14 is located in the center in the front, like the inclination angle θ of the ribs 23*a*, 23*b*, 23*c* and 23*d* mentioned above. It is also preferred that the width and intervals of the ribs 24*a*, 24*b*, 24*c* and 24*d* are set in the same way as the ribs 23*a*, 23*b*, 23*c* and 23*d* of the embodiment described above.

The two kinds of knee supporters of the embodiments shown in FIG. 5 and FIG. 8 can be used independently, or they can be used as a pair to be individually fitted on the right and left knees. When the two kinds of knee supporters are used as a pair when one of the knees has a pain, one of the supporters which has a remarkable effect to reduce the pain is fitted on the painful knee and the other is fitted on the other knee.

Figure 9:
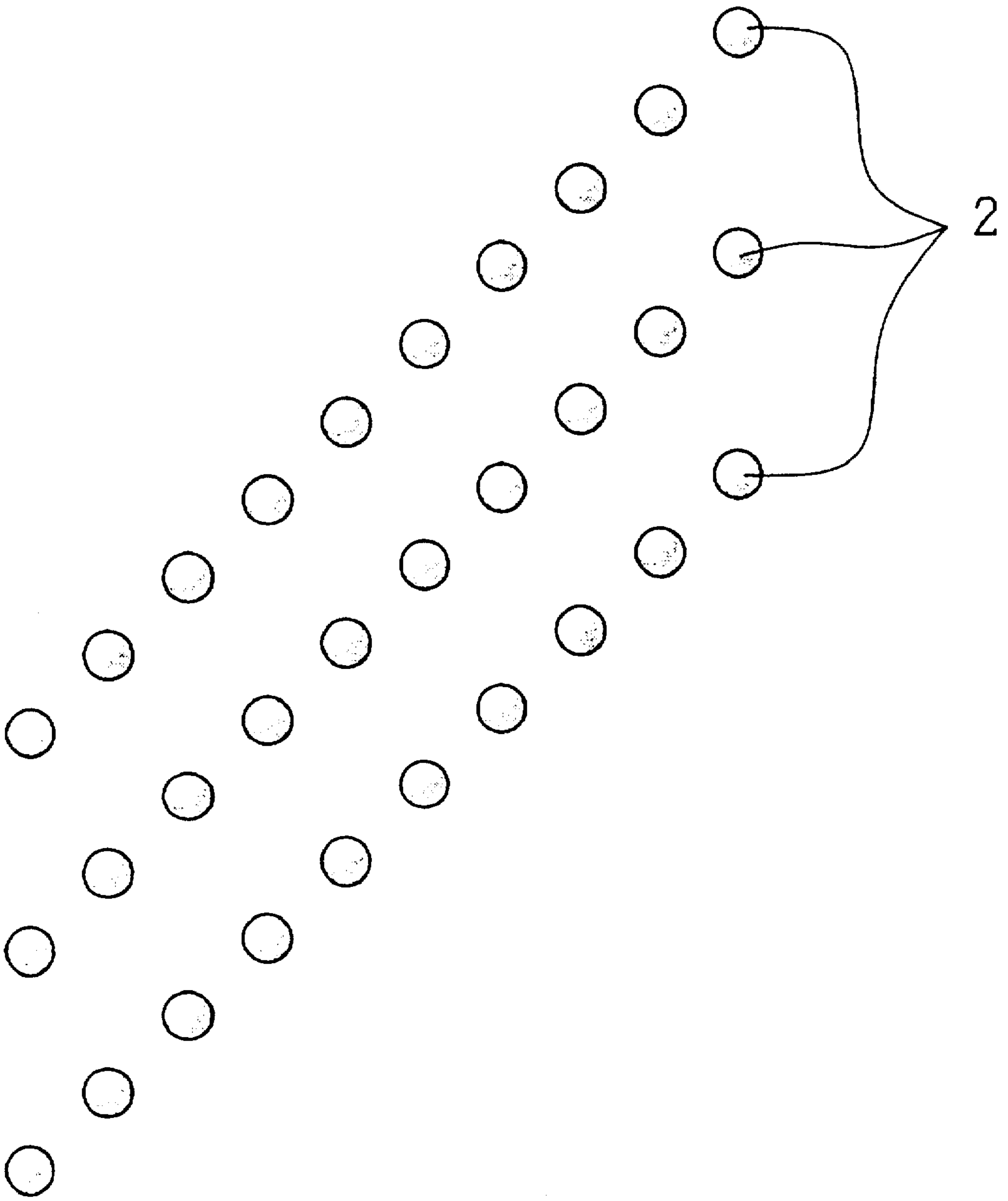
FIG. 9 is a diagram for illustrating a modification of the projection 2 formed on the knee supporters of the embodiments shown in FIG. 5 and FIG. 8.

Although the linearly raised ribs 23*a*, 23*b*, 23*c* and 23*d* and the ribs 24*a*, 24*b*, 24*c* and 24*d* are used as the projection 2 constituting the invention in the knee supporters explained above, small-hemispherical projections 2, 2 may be arranged in lines at certain intervals, as shown in FIG. 9.

Figure 11:
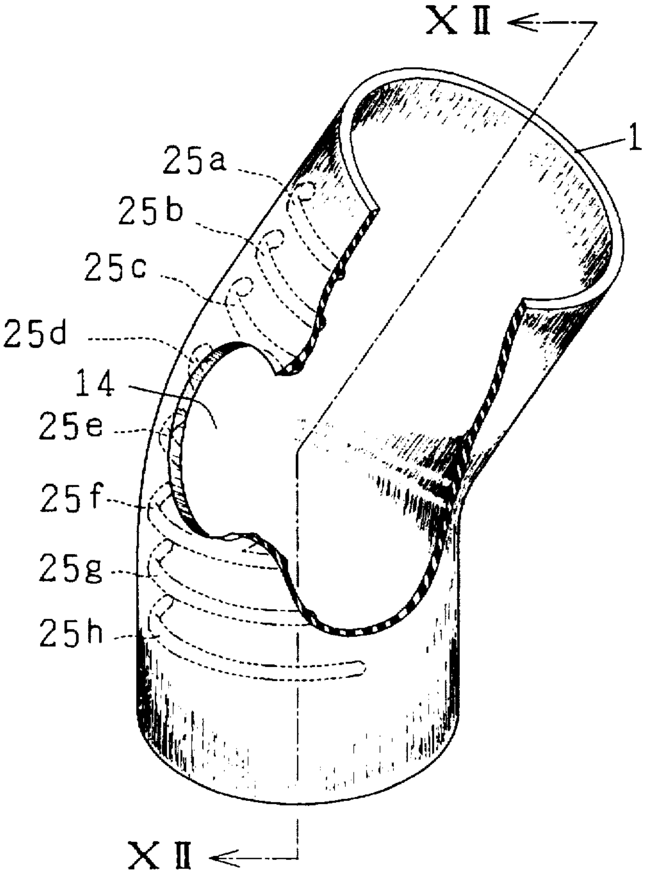
FIG. 11 is a partially broken perspective view of a knee supporter according to a fifth embodiment of the present invention.

FIG. 11 shows a knee supporter according to a fifth embodiment of the present invention, in which the entire shape of the band body 1 having elasticity is bent at about the center when viewed from the side.

In this supporter, linear ribs 25*a*–25*h* (formed of elastic silicone resin) formed on the inner surface on the front side where the through hole 14 is formed (the surface which comes in contact with the region around the kneecap when attached) extend in the inner circumferential direction of the band body 1. Accordingly, when the band body 1 is worn on the knee, the ribs 25*a*–25*h* are in contact with the outer surface of the leg in its circumferential direction (the direction along the periphery of a cross-section of the leg which is perpendicular to the center axis of the leg.)

Figure 12:
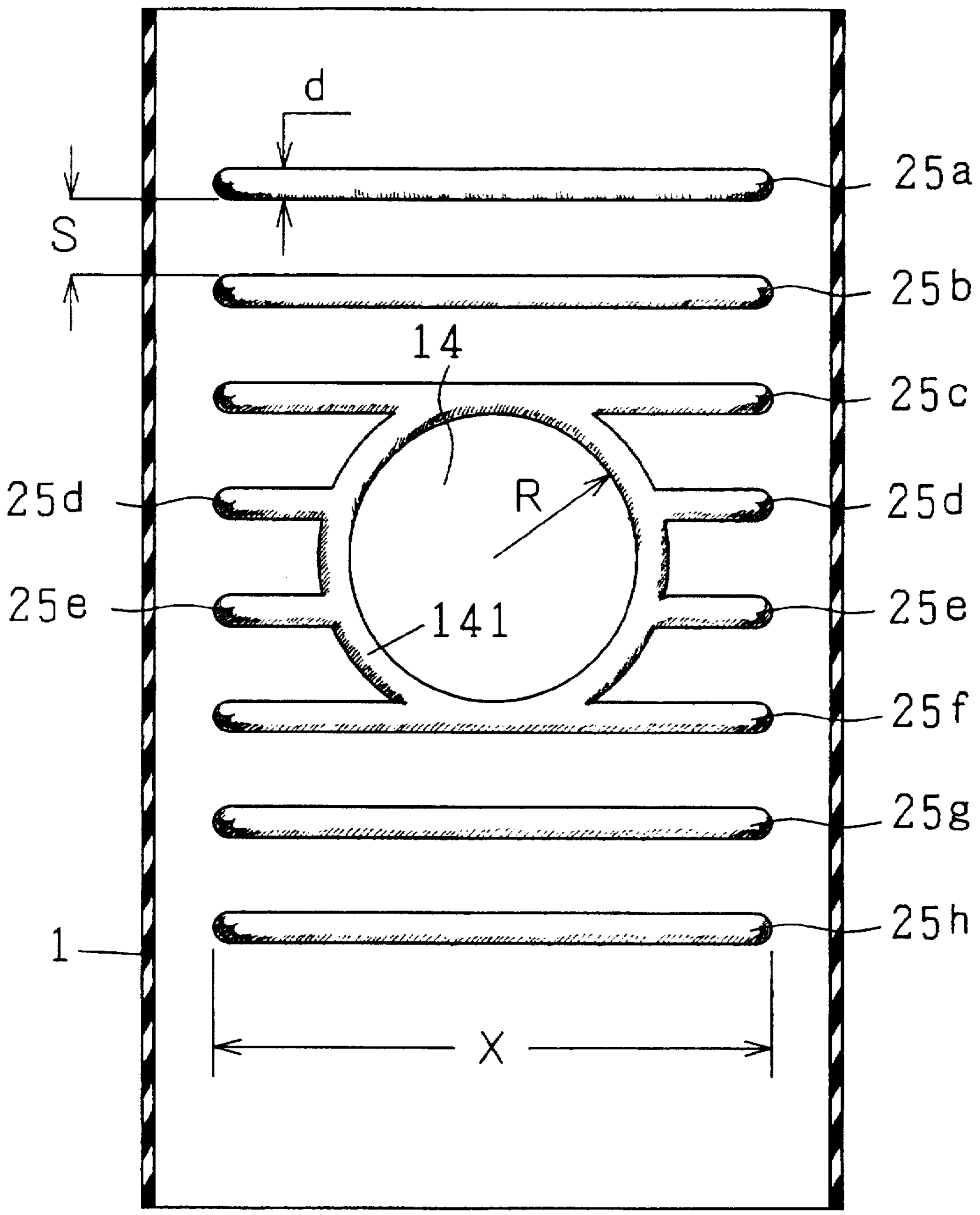
FIG. 12 is a cross-sectional view taken along the line XII—XII in FIG. 11.

FIG. 12 is a cross-sectional view taken along the line XII—XII in FIG. 11, which shows the front part of the band body 1 when it is cut into the front and rear parts along the section including the center line of the band body 1 in FIG. 11.

A circular rib 141 is formed around the through hole 14 on the inner surface of the band body 1 and ribs 25*c* and 25*f* extend in contact with the upper and lower parts of the periphery of the through hole 14. Between these ribs 25*c* and 25*f*, ribs 25*d* and 25*e* are formed in the positions which equally divide the diameter of the through hole 14 into thirds and extend in the lateral direction from the circular rib 141. Above the rib 25*c* and under the rib 25*f*, ribs 25*a* and 25*b* and ribs 25*g* and 25*h* are formed in parallel to them The width d of the ribs 25*a*–25*h* and the circular rib 141 is preferably set to about 5 to 7 mm, and is set to 7 mm in this embodiment. Preferably, the intervals S between the ribs 25*a*–25*c* and the ribs 25*f*–25*h* are set in the range of 10 to 15 mm, and are set to 15 mm in this embodiment. The length X between both ends of the ribs 25*a*–25*h* is preferably set in the range of 10 to 15 cm, and is set to 10 cm in this embodiment. The radius of the through hole 14 is preferably set in the range of 3 to 4 cm.

In the knee supporter shown in FIG. 11 and FIG. 12, the ribs 25*a*–25*h* press the region around the patella and the ribs 25*a*–25*h* come in contact with the outer surface of the leg in its circumferential direction. Therefore, it can be applied to a disease having a different condition from that to which the supporter having the ribs inclined with respect to the length direction of the band body 1 according to the embodiment of FIG. 8 is applied.

Figure 13:
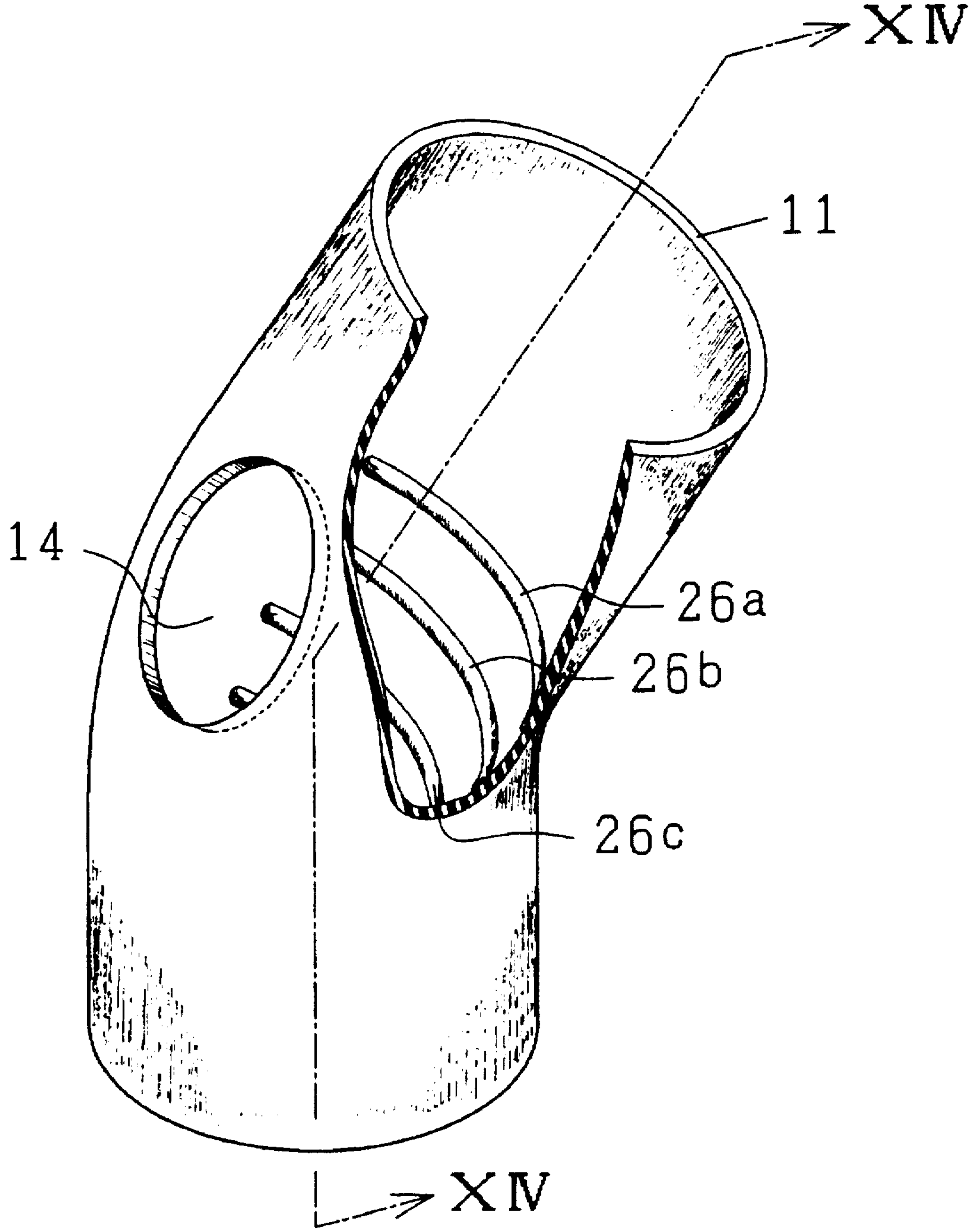
FIG. 13 is a partially broken perspective view of a knee supporter according to a sixth embodiment of the present invention.

FIG. 13 shows a knee supporter according to a sixth embodiment of the present invention, in which the entire form of the band body 1 having elasticity is bent approximately at the center, when seen from the side.

In this supporter, linear ribs 26*a*–26*e* formed on the inner surface opposite to the through hole 14 (the surface which comes in contact with the back side of the knee when attached) extend in the inner circumference direction of the band body 1. Accordingly, when the band body 1 is worn around the knee, the ribs 26*a*–26*e* formed of elastic silicone resin are in contact with the back of the knee in its circumferential direction.

Figure 14:
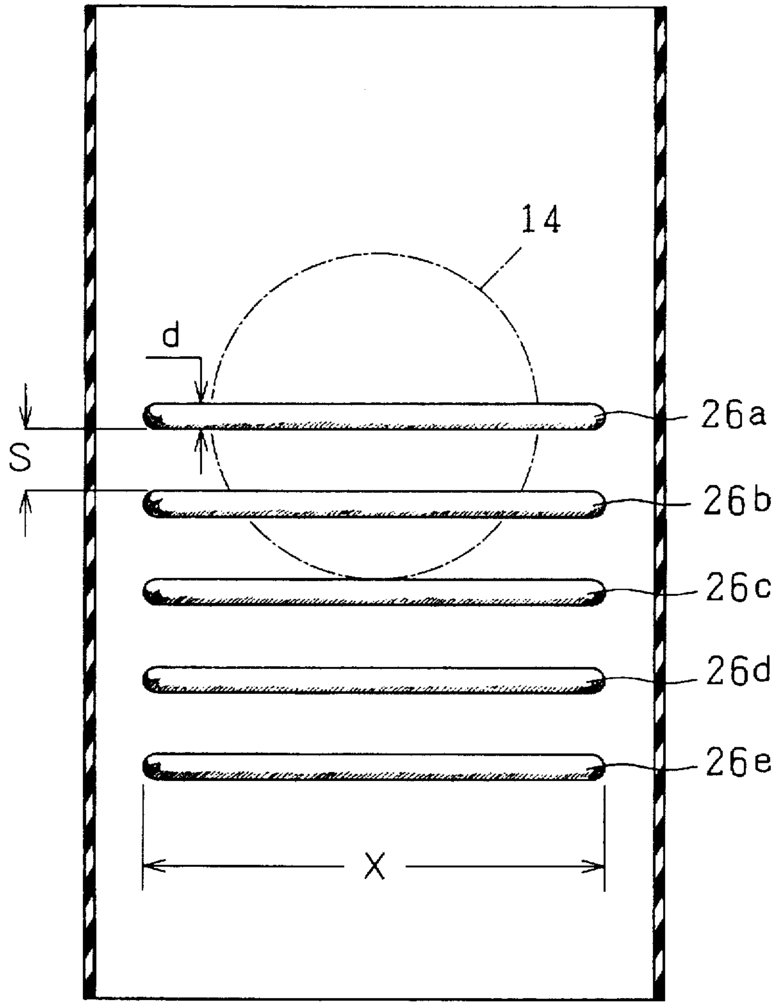
FIG. 14 is a cross-sectional view taken along the line XIV—XIV in FIG. 13.
Figure 15:
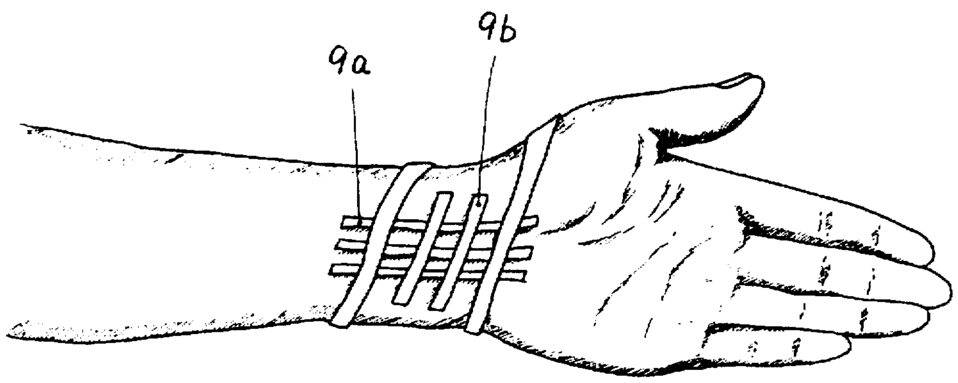
FIG. 15 PRIOR ART
FIG. 15 is a diagram showing the conventional taping technique applied on the wrist.

FIG. 14 is a cross-sectional view taken along the line XIV—XIV in FIG. 13, which shows the back part of the band body 1 when it is cut into the front and back parts along the section including the center line of the band body 1 in FIG. 13.

A rib 26*c* is provided in the position facing the lower end of the inner circumference of the through hole 14 formed in the front of the band body 1. On both sides of the rib 26*c*, ribs 26*a*, 26*b*, 26*d* and 26*e* are formed in parallel to it. The width d, the intervals S and the distance X between the two ends of the ribs 26*a*–26*e* are set to the same dimensions as those of the ribs 25*a*–25*h* provided on the front side of the band body 1 in the previous embodiment.

In the knee supporter shown in FIG. 13 and FIG. 14, the ribs 26*a*–26*e* apply pressure to the back of the knee and the ribs 26*a*–26*e* come in contact with the outer surface of the leg in its circumferential direction when worn on the knee. Therefore, it can be applied to a problem having a different condition from that to which the supporter of the embodiment shown in FIG. 5 to FIG. 7 having the ribs inclined with respect to the length direction of the band body 1 is applied.

Similar to the supporters of the embodiments shown in FIG. 5 and FIG. 8, the two kinds of knee supporters shown in FIG. 11 and FIG. 13 can be independently used, or they can be used as a pair to be individually fitted on the right and left knees. It goes without saying that the small-hemispherical projections 2, 2 shown in FIG. 9 can be used in place of the ribs *25a–25h* and the ribs *26a–26e*.

In any of the knee supporters of the embodiments shown in FIG. 5, FIG. 8, FIG. 11 and FIG. 13, the raised height of the ribs serving as the projection 2 is set to about 1 mm, similar to that according to the embodiment of FIG. 1. Sewing both edges of the band body 1 and the inner periphery of the through hole 14 prevents the fibers from fraying.

Although the supporters have been described as being applied to the knees in the embodiments of FIG. 5, FIG. 8, FIG. 11 and FIG. 13, they can be used as supporters for elbows. In this case, the supporter is fitted around the elbow in such a manner that the through hole 14 formed in the band body 1 is located on the outside of the bending part of the elbow.

Although the embodiments above have illustrated the application of the present invention to wrist bands and joint supporters, the projections explained above may be formed on the inner surface of a simple cylindrical supporter and it may be applied to a region other than the joints, such as the thigh, the upper arm, the waist, etc.

In the wrist bands according to the embodiments of FIG. 1 and FIG. 4, the projections 2 may include one rib and another rib intersecting each other to form one intersection. The supporters according to the embodiments of FIG. 5, FIG. 8, FIG. 11 and FIG. 13 may include only one linear rib.

The projections 2 of the knee supporters according to the embodiments of FIG. 5, FIG. 8, FIG. 11 and FIG. 13 may be formed like a lattice similar to the embodiments of FIG. 1 and FIG. 4. The projections 2 of the wrist bands according to the embodiments of FIG. 1 and FIG. 4 may be formed as parallel linear ribs like the embodiments of FIG. 5, FIG. 8, FIG. 11 and FIG. 13.

Furthermore, thick cloth tape having elasticity may be sewn on the inner surface of the band body 1 forming a wrist band or a knee supporter to serve as the ribs described above.

While the invention has been described in detail, the foregoing description is in all aspects illustrative and not restrictive. It is understood that numerous other modifications and variations can be devised without departing from the scope of the invention.

What is claimed is:

1. A health promoting implement comprising:

a band body which is positionable on a body of a user in a freely fitted and removable manner to surround a part of the body, and so that an inner surface thereof faces the body, said band body having a through hole which fits around a projecting part, such as a bending part of a bent elbow and a knee cap; and a projection provided on the inner surface of said band body, said projection including at least one linear rib.

2. The health promoting implement according to claim 1, wherein said band body includes a cylindrical body composed of cloth having elasticity.

3. The health promoting implement according to claim 2, wherein said cylindrical body is formed to have a bend in a center region thereof.

4. The health promoting implement according to claim 1, wherein said band body is a flexible band body having two ends, and includes a male member and a female member of a plane fastener formed on the respective ends of said band body, said male member and said female member being couplable together in an overlapped state to hold said band body to the body of the user.

5. The health promoting implement according to claim 1, wherein said linear rib extends in a same direction as a direction in which said band body is wound on the body.

6. The health promoting implement according to claim 1, wherein said linear rib extends in a direction substantially spirally winding on the body.

7. The health promoting implement according to any of claim 1, further comprising positioning means for positioning said projection in a position where it abuts on the body.

8. The health promoting implement according to claim 7, wherein said positioning means includes a through hole which is formed in said band body and fits around a projecting part, such as a bending part of a bent elbow and a kneecap.

9. The health promoting implement according to claim 8, wherein said projection is provided on the inner surface of said band body in a region opposing the through hole.

10. The health promoting implement according to claim 1, further comprising positioning means for positioning said projection in a position where it adapts to be fitted on the body, said positioning means including a circular rib which is formed on the inner surface of said band body and fitting around a projecting part of the body, such as a bending part of a bent elbow and a knee cap.

11. The health promoting implement according to claim 1, wherein said projection comprises at least one linear rib having a constant width between about 5 mm and 7 mm, and a length between about 10 cm and 15 cm.

12. The health promoting implement according to claim 11, wherein said at least one linear rib has a hemispherical cross-sectional profile.

13. A health promoting implement, comprising:

a band body which is positionable on a body of a user in a freely fitted and removable manner to surround a part of the body, and so that an inner surface thereof faces the body; and a projection provided on the inner surface of said band body, said projection including two linear ribs intersecting each other.

14. The health promoting implement according to claim 13, wherein said band body includes a cylindrical body composed of cloth having elasticity.

15. The health promoting implement according to claim 13, wherein said cylindrical body is formed to have a bend in a center region thereof.

16. The health promoting implement according to claim 13, wherein said band body is a flexible band body having two ends, and includes a male member and a female member of a plane fastener formed on the respective ends of said band body, said male member and said female member being couplable together in an overlapped state to hold said band body to the body of the user.

17. A health promoting implement, comprising:

a band body which is positionable on a body of a user in a freely fitted and removable manner to surround a part of the body, and so that an inner surface thereof faces the body, said band body extending along an axis when surrounding the part of the body, said band body having a through hole which fits around a projecting part, such as a bending part of a bent elbow and a knee cap; and a projection provided on the inner surface of said band body, said projection including at least two linear ribs extending parallel to each other and being respectively spaced from each other in a direction of the axis.

18. The health promoting implement according to claim 17, wherein said band body includes a cylindrical body composed of cloth having elasticity.

19. The health promoting implement according to claim 18, wherein said cylindrical body is formed to have a bend in a center region thereof.

20. The health promoting implement according to claim 17, wherein said band body is a flexible band body having two ends, and includes a male member and a female member of a plane fastener formed on the respective ends of said band body, said male member and said female member being couplable together in an overlapped state to hold said band body to the body of the user.

21. The health promoting implement of claim 17, wherein each of said linear ribs has a constant width between about 5 mm and 7 mm, and a length between about 10 cm and 15 cm.

22. The health promoting implement according to claim 17, wherein each of said linear ribs has a hemispherical cross-sectional profile.

23. A health promoting implement, comprising:

a band body which is positionable on a body of a user in a freely fitted and removable manner to surround a part of the body, and so that an inner surface thereof faces the body;

a projection provided on the inner surface of said band body, said projection including at least one linear rib; and positioning means for positioning said projection in a position where it adapts to be fitted on the body, said positioning means including a through hole which is formed in said band body and fits around a projecting part, such as a bending part of a bent elbow and a knee cap, wherein said projection is formed on the inner surface of said band body in a region surrounding the through hole.

24. The health promoting implement according to claim 23, wherein said positioning means further comprises a circular rib formed on a periphery of the through hole and on the inner surface of said band body.

25. The health promoting implement according to claim 24, wherein said at least one linear rib comprises a plurality of linear ribs arranged parallel to each other in the region surrounding the through hole.

26. The health promoting implement according to claim 25, wherein each of said plurality of linear ribs is positioned to a side of a respective adjacent one of said plurality of linear ribs at a constant interval.

27. The health promoting implement according to claim 23, wherein said at least one linear rib has a constant width between about 5 mm and 7 mm, and a length between about 10 cm and 15 cm.

28. The health promoting implement according to claim 23, wherein said at least one linear rib has a hemispherical cross-sectional profile.

* * * * *